United States Patent
Ishii et al.

(10) Patent No.: US 10,842,446 B2
(45) Date of Patent: Nov. 24, 2020

(54) MEDICAL INFORMATION PROCESSING APPARATUS, X-RAY CT APPARATUS, AND MEDICAL INFORMATION PROCESSING METHOD

(71) Applicant: Toshiba Medical Systems Corporation, Otawara (JP)

(72) Inventors: Hideaki Ishii, Nasushiobara (JP); Takuya Sakaguchi, Utsunomiya (JP); Kazumasa Arakita, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 650 days.

(21) Appl. No.: 15/613,461

(22) Filed: Jun. 5, 2017

(65) Prior Publication Data

US 2017/0347973 A1    Dec. 7, 2017

(30) Foreign Application Priority Data

Jun. 6, 2016  (JP) ................................ 2016-112972
May 16, 2017 (JP) ................................ 2017-097459

(51) Int. Cl.
 *A61B 6/03* (2006.01)
 *A61B 6/00* (2006.01)
 (Continued)

(52) U.S. Cl.
 CPC ............... *A61B 6/03* (2013.01); *A61B 6/463* (2013.01); *A61B 6/488* (2013.01); *A61B 6/5217* (2013.01);
 (Continued)

(58) Field of Classification Search
 CPC ......... A61B 6/5235; A61B 6/03; A61B 6/463; A61B 6/488; A61B 6/5217; A61B 6/12;
 (Continued)

(56) References Cited

U.S. PATENT DOCUMENTS 6,238,345 B1 * 5/2001 Wissler ............... G01S 7/52036
                                                       600/443
6,373,970 B1 * 4/2002 Dong ........................ G06K 9/32
                                                       128/922

(Continued)

FOREIGN PATENT DOCUMENTS

| JP | 2009-142300 | 7/2009 |
| JP | 2009-195586 | 9/2009 |
| JP | 2013-172793 | 9/2013 |

*Primary Examiner* — Bo Joseph Peng
(74) *Attorney, Agent, or Firm* — Oblon, McClelland, Maier & Neustadt, L.L.P.

(57) ABSTRACT

A medical information processing apparatus according to an embodiment includes processing circuitry. The processing circuitry collects pieces of past image data in a plurality of time phases that contain at least a part of a coronary artery of a heart and new image data in one time phase that contains at least a part of the coronary artery and has been acquired after acquisition of the pieces of past image data. The processing circuitry performs registration processing between the pieces of collected past image data and registration processing between any one of the pieces of past image data and the new image data. The processing circuitry generates pieces of synthesized image data corresponding to the time phases of the pieces of past image data other than the past image data on which the registration processing with the new image data has been executed by reflecting a shape of the new image data based on results of the registration processing. The processing circuitry derives a fluid parameter related to the coronary artery by executing fluid analysis using the pieces of synthesized image data.

11 Claims, 11 Drawing Sheets

(51) Int. Cl.
*A61B 5/00* (2006.01)
*A61B 8/06* (2006.01)
*A61B 8/08* (2006.01)
*A61B 5/02* (2006.01)
*A61B 5/026* (2006.01)
*A61B 6/12* (2006.01)

(52) U.S. Cl.
CPC ............ *A61B 6/5235* (2013.01); *A61B 5/026* (2013.01); *A61B 5/02007* (2013.01); *A61B 5/7282* (2013.01); *A61B 5/743* (2013.01); *A61B 6/12* (2013.01); *A61B 6/4035* (2013.01); *A61B 6/503* (2013.01); *A61B 6/507* (2013.01); *A61B 6/54* (2013.01); *A61B 8/06* (2013.01); *A61B 8/0883* (2013.01); *A61B 8/0891* (2013.01); *A61B 2576/00* (2013.01)

(58) Field of Classification Search
CPC ........... A61B 6/54; A61B 6/503; A61B 6/507; A61B 6/4035; A61B 5/026; A61B 5/7282; A61B 5/743; A61B 5/02007; A61B 2576/00; A61B 8/06; A61B 8/0883; A61B 8/0891
See application file for complete search history.

(56) References Cited

U.S. PATENT DOCUMENTS

| | | | |
|---|---|---|---|
| 2008/0193004 A1* | 8/2008 | Mine | A61B 6/5247 382/131 |
| 2008/0232714 A1* | 9/2008 | Nord | G06T 7/33 382/284 |
| 2009/0147909 A1 | 6/2009 | Yoda et al. | |
| 2012/0106704 A1* | 5/2012 | Maurer, Jr. | G06F 19/3481 378/65 |
| 2012/0121200 A1* | 5/2012 | Guetter | G06T 3/0068 382/248 |
| 2014/0253544 A1 | 9/2014 | Arakita et al. | |
| 2015/0117727 A1* | 4/2015 | Mohr | G06F 19/321 382/128 |

\* cited by examiner

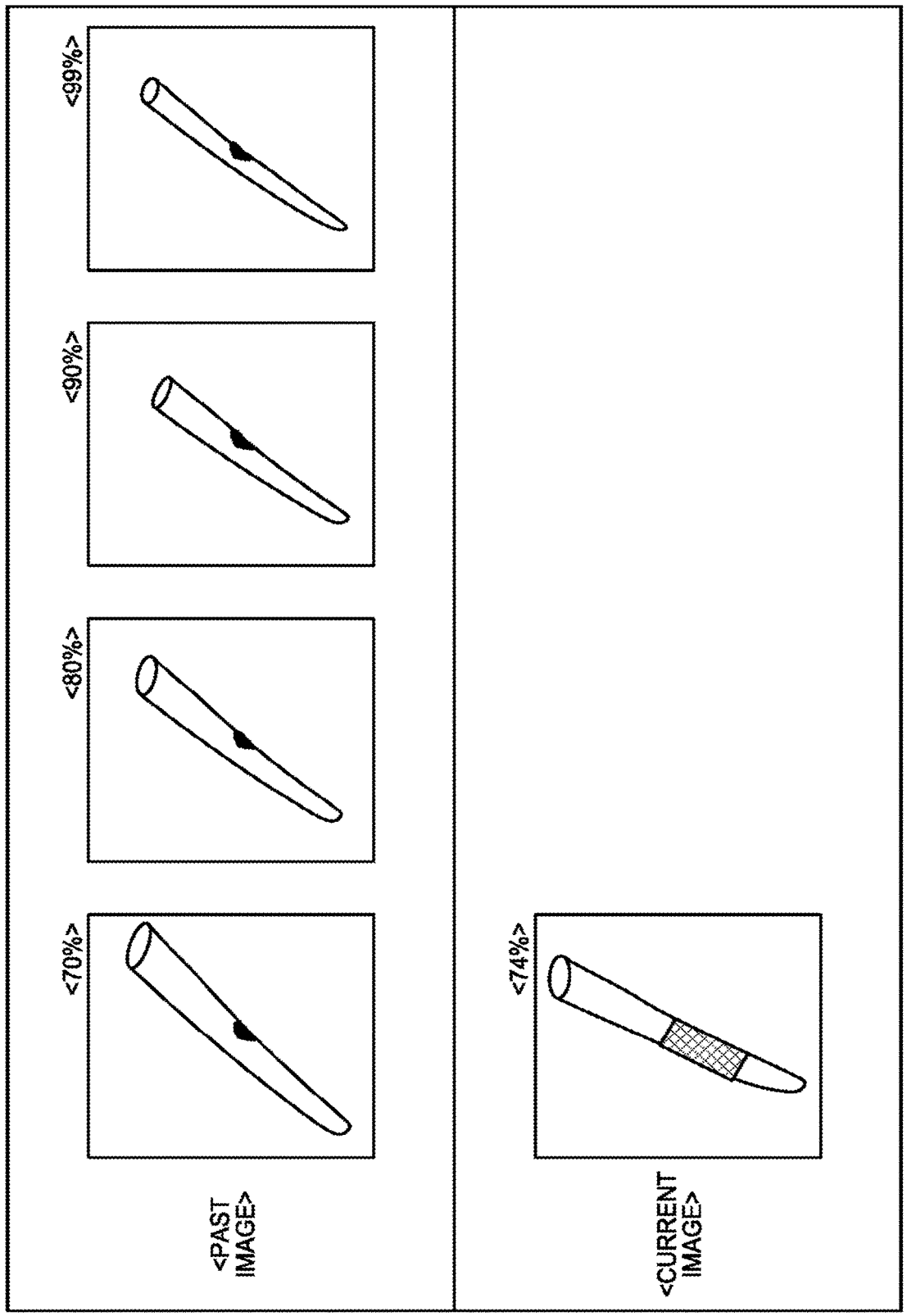

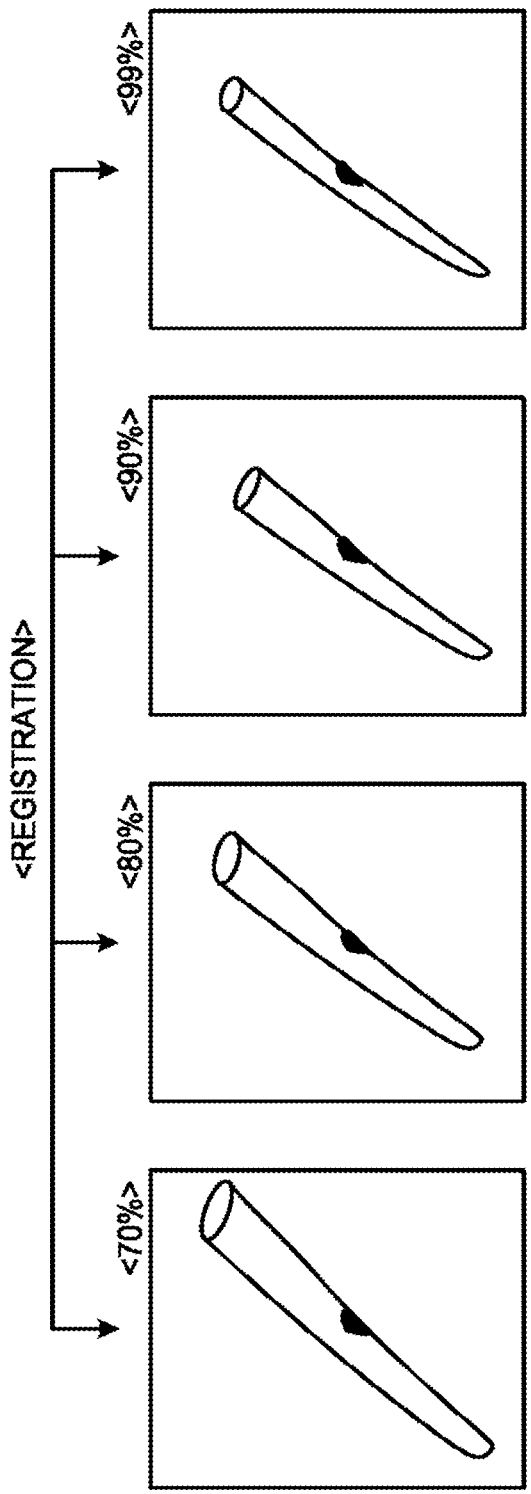

MEDICAL INFORMATION PROCESSING APPARATUS, X-RAY CT APPARATUS, AND MEDICAL INFORMATION PROCESSING METHOD

CROSS-REFERENCE TO RELATED APPLICATIONS

This application is based upon and claims the benefit of priority from Japanese Patent Application No. 2016-112972, filed on Jun. 6, 2016, and Japanese Patent Application No. 2017-97459, filed on May 16, 2017; the entire contents of which are incorporated herein by reference.

FIELD

Embodiments described herein relate generally to a medical information processing apparatus, an X-ray CT apparatus, and a medical information processing method.

BACKGROUND

Conventionally, it has been known that causes of ischemic diseases of organs are roughly classified into hematogenous disorder and functional disorder of the organs themselves. For example, stenosis as an example of coronary hematogenous disorder is a serious lesion leading to ischemic heart disease, and for the ischemic heart disease, it is necessary to determine whether pharmacological treatment or stent treatment should be performed, and so on. In recent years, as diagnosis with coronary hematogenous ischemia evaluation, a method in which a fractional flow reserve (FFR) is measured using a pressure wire in coronary angiography (CAG) with catheters is being recommended.

A method in which the coronary hematogenous ischemia is noninvasively evaluated using medical images of the heart that have been collected by a medical image diagnostic apparatus such as an X-ray computed tomography (CT) apparatus, a magnetic resonance imaging (MRI) apparatus, and an ultrasonic diagnostic apparatus has also been known. In recent years, the coronary hematogenous ischemia is evaluated by various methods as described above and treatment based on the evaluation is performed.

BRIEF DESCRIPTION OF THE DRAWINGS

FIG. 5 is a view for explaining an example of target images in the first embodiment;

FIG. 6A is a view for explaining an example of registration processing between past images in the first embodiment;

DETAILED DESCRIPTION

According to an embodiment, a medical information processing apparatus includes processing circuitry. The processing circuitry is configured to collect pieces of past image data in a plurality of time phases that contain at least a part of a coronary artery of a heart and new image data in one time phase that contains at least a part of the coronary artery and has been acquired after acquisition of the pieces of past image data. The processing circuitry is configured to perform registration processing between the pieces of collected past image data and registration processing between any one of the pieces of past image data and the new image data. The processing circuitry is configured to generate pieces of synthesized image data corresponding to the time phases of the pieces of past image data other than the past image data on which the registration processing with the new image data has been executed by reflecting a shape of the new image data based on results of the registration processing. The processing circuitry is configured to derive a fluid parameter related to the coronary artery by executing fluid analysis using the pieces of synthesized image data.

Hereinafter, embodiments of a medical information processing apparatus, an X-ray CT apparatus, and a medical information processing method according to the present application will be described in detail with reference to the accompanying drawings. The following embodiments do not limit the medical information processing apparatus, the X-ray CT apparatus, and the medical information processing program according to the present application.

First Embodiment

First, a first embodiment is described. The first embodiment describes an example in which a technology disclosed by the present application is applied to a medical information processing apparatus. A medical information processing system including the medical information processing apparatus is described below, as an example. The case in which a blood vessel of the heart is subject to analysis is described below, as an example.

Figure 1:
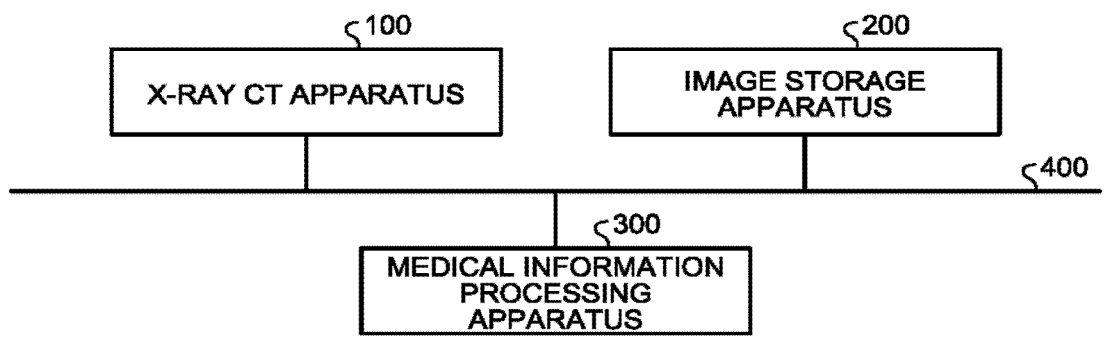
FIG. 1 is a diagram illustrating an example of the configuration of a medical information processing system according to a first embodiment.

FIG. 1 is a diagram illustrating an example of the configuration of the medical information processing system in the first embodiment. As illustrated in FIG. 1, the medical information processing system in the first embodiment includes an X-ray computed tomography (CT) apparatus 100, an image storage apparatus 200, and a medical information processing apparatus 300.

For example, the medical information processing apparatus 300 in the first embodiment is connected to the X-ray CT apparatus 100 and the image storage apparatus 200 through a network 400, as illustrated in FIG. 1. It should be noted that the medical information processing system may be further connected to other medical image diagnostic apparatuses such as an MRI apparatus, an ultrasonic diagnostic apparatus, and a positron emission tomography (PET) apparatus through the network 400.

The X-ray CT apparatus 100 collects CT image data (volume data) of a subject. To be specific, the X-ray CT apparatus 100 rotationally moves an X-ray tube and an X-ray detector substantially about a subject and detects X rays that have passed through the subject to collect pieces of projection data. Then, the X-ray CT apparatus 100 generates time-series three-dimensional CT image data based on the collected pieces of projection data.

The image storage apparatus 200 archives therein pieces of image data collected by various medical image diagnostic apparatuses. The image storage apparatus 200 is implemented by, for example, a computer apparatus such as a server apparatus. In the embodiment, the image storage apparatus 200 acquires the CT image data (volume data) from the X-ray CT apparatus 100 through the network 400, and stores the acquired CT image data in memory circuitry provided in the apparatus or at the outside of the apparatus.

The medical information processing apparatus 300 acquires the pieces of image data from various medical image diagnostic apparatuses through the network 400 and processes the pieces of acquired image data. The medical information processing apparatus 300 is implemented by, for example, a computer apparatus such as a workstation. In the embodiment, the medical information processing apparatus 300 acquires the CT image data from the X-ray CT apparatus 100 or the image storage apparatus 200 through the network 400, and performs various pieces of image processing on the acquired CT image data. Then, the medical information processing apparatus 300 displays the CT image data before or after the pieces of image processing are performed on a display or the like.

Figure 2:
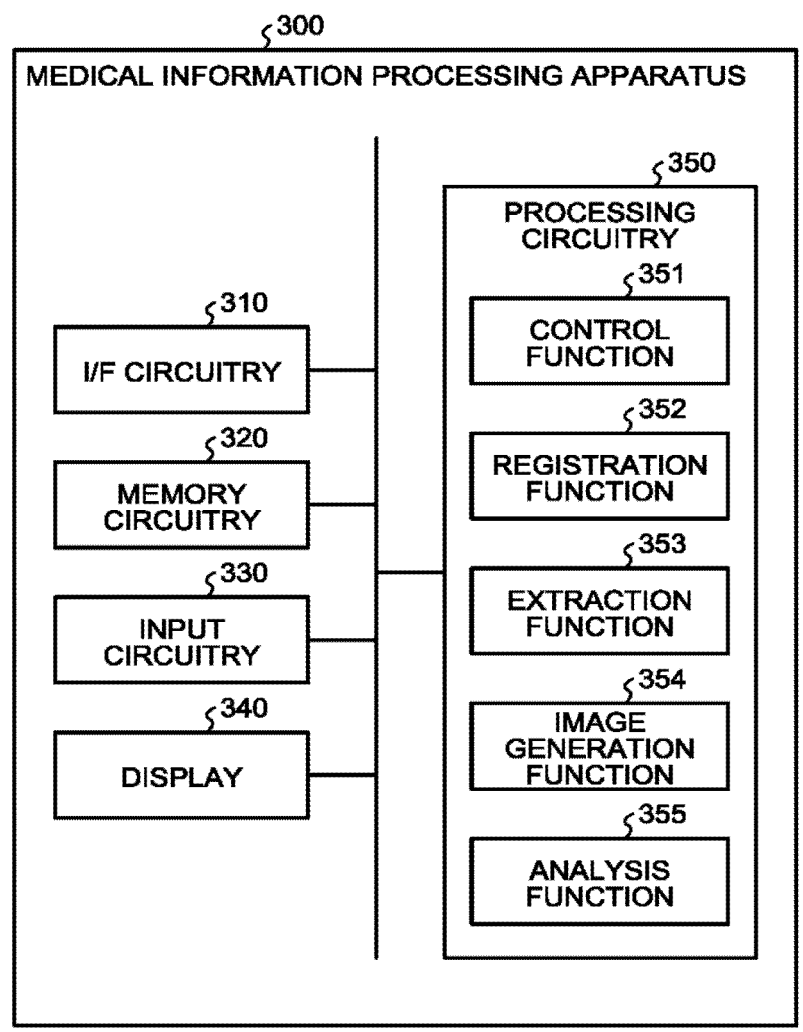
FIG. 2 is a diagram illustrating an example of the configuration of a medical information processing apparatus in the first embodiment.

FIG. 2 is a diagram illustrating an example of the configuration of the medical information processing apparatus 300 in the first embodiment. As illustrated in FIG. 2, the medical information processing apparatus 300 includes, for example, interface (I/F) circuitry 310, memory circuitry 320, input circuitry 330, a display 340, and processing circuitry 350.

The I/F circuitry 310 is connected to the processing circuitry 350 and controls transmission and communication of various pieces of data to and with various medical image diagnostic apparatuses or the image storage apparatus 200 connected through the network 400. The I/F circuitry 310 is implemented by, for example, a network card, a network adaptor, or a network interface controller (NIC). In the embodiment, the I/F circuitry 310 receives the CT image data from the X-ray CT apparatus 100 or the image storage apparatus 200, and outputs the received CT image data to the processing circuitry 350.

The memory circuitry 320 is connected to the processing circuitry 350, and stores therein various pieces of data. The memory circuitry 320 is implemented by, for example, a semiconductor memory element such as a random access memory (RAM) and a flash memory, a hard disk, or an optical disk. In the embodiment, the memory circuitry 320 stores therein the CT image data received from the X-ray CT apparatus 100 or the image storage apparatus 200.

The input circuitry 330 is connected to the processing circuitry 350, converts an input operation received from an operator to an electric signal, and outputs it to the processing circuitry 350. The input circuitry 330 is implemented by, for example, a track ball, a switch button, a mouse, a keyboard, or a touch panel.

The display 340 is connected to the processing circuitry 350 and displays various pieces of information and various pieces of image data that are output from the processing circuitry 350. The display 340 is implemented by, for example, a liquid crystal monitor, a cathode ray tube (CRT) monitor, or a touch panel.

The processing circuitry 350 controls the respective components included in the medical information processing apparatus 300 in accordance with the input operation received through the input circuitry 330 from the operator. The processing circuitry 350 is implemented by, for example, a processor. In the embodiment, the processing circuitry 350 controls to store the CT image data output from the I/F circuitry 310 in the memory circuitry 320. The processing circuitry 350 reads the CT image data from the memory circuitry 320, and displays it on the display 340.

With this configuration, the medical information processing apparatus 300 in the embodiment can reduce an exposure dose in follow-up. To be specific, the medical information processing apparatus 300 reduces the exposure dose in the follow-up by using medical images collected in the past when index values related to blood flow are calculated by fluid analysis using medical images (for example, three-dimensional CT image data) containing a blood vessel. The medical information processing apparatus 300, for example, executes, in the follow-up, the fluid analysis using a medical image in one time phase that has been newly collected and medical images in three time phases that have been collected in the past when pieces of data in four time phases are used for the fluid analysis. It is therefore sufficient that the new medical image for only one time phase is collected, thereby reducing the exposure dose.

Examples of the index values related to the blood flow include a fractional flow reserve (FFR), dynamic indexes in the blood vessel, and indexes related to a blood flow rate. The FFR is a ratio between a pressure at a proximal portion in the blood vessel that is close to the heart and a pressure at a distal portion that is distanced from the heart and is expressed by, for example, "FFR=Pd (pressure at the distal portion)/Pa (pressure at the proximal portion)". When stenosis (treatment target site) is generated in the blood vessel, the pressure at the distal portion is lowered due to the stenosis and a value of the FFR is therefore lowered. The fluid analysis is used for determining whether treatment is necessary by calculating the value of the FFR and the like. Examples of the dynamic indexes in the blood vessel include a pressure, a vector, and a shear stress. Examples of the indexes related to the blood flow rate include a flow rate and a flow velocity.

Hereinafter, the first embodiment describes the case in which pieces of CT image data in four time phases are used in the fluid analysis for the coronary artery as a target, as an example. As illustrated in FIG. 2, the processing circuitry 350 in the embodiment executes a control function 351, a registration function 352, an extraction function 353, an image generation function 354, and an analysis function 355. The processing circuitry 350 is an example of processing circuitry in the scope of the claims.

First, the fluid analysis by the analysis function 355 is described. The analysis function 355 executes the fluid analysis based on the pieces of CT image data. To be specific, the analysis function 355 extracts pieces of time-series vascular shape data representing the shape of the blood vessel from the pieces of three-dimensional CT image data. The analysis function 355 extracts the pieces of time-series vascular shape data by, for example, reading the pieces of CT image data in a plurality of time phases that have been collected with time from the memory circuitry 320, and performing the pieces of image processing on the pieces of read CT image data in the time phases.

The analysis function 355 sets a target region for which the index values are calculated to a vascular region contained in each of the pieces of CT image data. To be specific, the analysis function 355 sets the target region to the vascular region based on an instruction through the input circuitry 330 by the operator or image processing. Then, the analysis function 355 extracts, as the pieces of vascular shape data of the set target region, a core line of the blood vessel (coordinate information of the core line), cross-sectional areas of the blood vessel and the lumen in a cross section perpendicular to the core line, a distance from the core line to an inner wall and a distance from the core line to an outer wall in a columnar direction in the cross section perpendicular to the core line, and the like from each of the pieces of CT image data. It should be noted that the analysis function 355 can extract various other pieces of vascular shape data depending on analysis methods.

Furthermore, the analysis function 355 sets analysis conditions of the fluid analysis. To be specific, the analysis function 355 sets, as the analysis conditions, physical property values of blood, conditions of iterative calculation, initial values for analysis, and the like. The analysis function 355 sets, as the physical property values of the blood, a viscosity, a density, and the like of the blood, for example. The analysis function 355 sets, as the conditions of the iterative calculation, a maximum number of times of iteration in the iterative calculation, a relaxation coefficient, a residue allowable value, and the like. The analysis function 355 sets, as the initial values for analysis, initial values of the flow rate, the pressure, a fluid resistance, a pressure boundary, and the like. Various values that are used by the analysis function 355 may be incorporated in the system in advance, or may be defined by the operator interactively.

The analysis function 355 sets a treatment target site in the blood vessel in each of the pieces of image data. To be specific, the analysis function 355 sets the treatment target site in the blood vessel manually or automatically. The analysis function 355 sets, for example, a range received through the input circuitry 330 as the treatment target site. In such a case, the input circuitry 330 receives the range (treatment target site) for which the analysis conditions are changed and the analysis function 355 sets the received range as the treatment target site. Alternatively, the analysis function 355 automatically sets the treatment target site based on the shape in the target region. The analysis function 355, for example, extracts stenosis portions based on the shape in the target region and sets, as the treatment target site, a stenosis portion having equal to or higher than a constant stenosis degree among the extracted stenosis portions. The stenosis portions can be extracted by a desired method.

The analysis function 355 calculates the index values related to the blood flow of the blood vessel by the fluid analysis using each of the pieces of image data containing the blood vessel. To be specific, the analysis function 355 executes the fluid analysis using the pieces of vascular shape data and the analysis conditions and calculates the index values related to the blood flow in the target region of the blood vessel. The analysis function 355 calculates the index values of the pressure, the blood flow rate, the blood flow velocity, the vector, the shear stress, and the like at each of predetermined positions of the blood vessel based on the pieces of vascular shape data such as the contours of the lumen and the outer wall of the blood vessel and the cross-sectional area and the core line of the blood vessel, and the set conditions such as the physical property values of blood, the conditions of the iterative calculation, and the initial values for analysis. The analysis function 355 further calculates the index values of the FFR and the like from the calculated index values.

Figure 3:
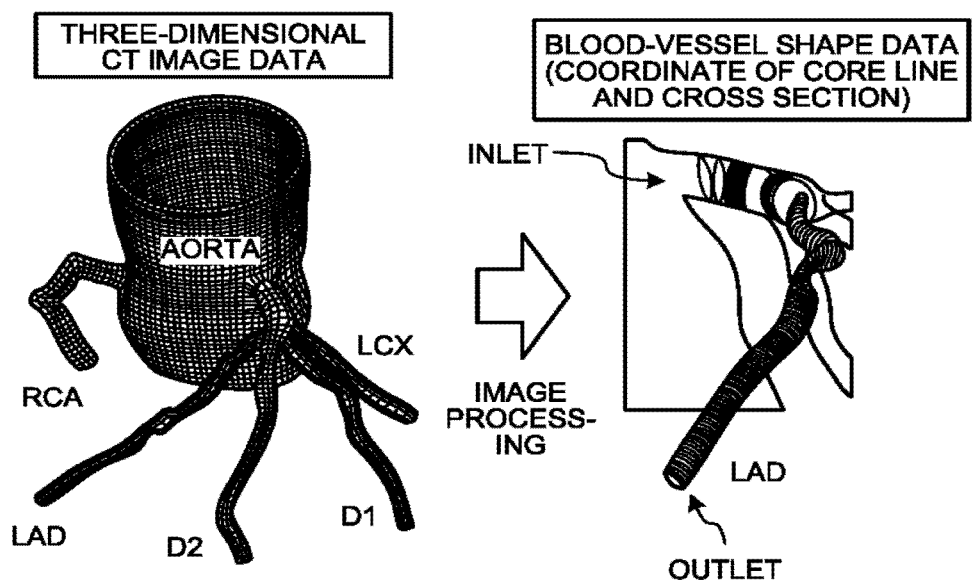
FIG. 3 is a view for explaining an example of processing by an analysis function in the first embodiment.

FIG. 3 is a view for explaining an example of processing by the analysis function 355 in the first embodiment. As illustrated in FIG. 3, the analysis function 355, for example, extracts the pieces of vascular shape data including the coordinates of the core line and the cross section information for the left anterior descending artery (LAD) as the target region from the three-dimensional CT image data containing an aorta and the coronary artery. The analysis function 355 sets the analysis conditions of analysis for the extracted LAD as the target. Then, the analysis function 355 performs the fluid analysis using the pieces of vascular shape data of the extracted LAD and the set conditions to calculate the index values of the pressure, the blood flow rate, the blood flow velocity, the vector, the shear stress, and the like at each of the predetermined positions along the core line from the boundary of an inlet of the target region LAD to the boundary of an outlet thereof, for example. That is to say, the analysis function 355 calculates distributions of the pressure, the blood flow rate, the blood flow velocity, the vector, the shear stress, and the like for the target region. Then, the analysis function 355 calculates the FFR at each of the positions in the target region based on the calculated distribution in pressure, for example.

As described above, the analysis function 355 extracts the pieces of vascular shape data from each of the pieces of CT image data in the time phases that have been collected with time and performs the fluid analysis using the extracted pieces of vascular shape data in the time phases and the analysis conditions to calculate the index values related to the blood flow. The analysis function 355 thus executes the fluid analysis using the pieces of CT image data in the time phases in order to enhance accuracy of a result by the fluid analysis. In order to provide the analysis result with high accuracy, the pieces of CT image data in the time phases that involve variation in the shape of the coronary artery (for example, variation in the cross-sectional area) as large as possible and less motion with beating are desirably used. That is to say, the pieces of CT image data in the time phases providing the pieces of time-series vascular shape data that have a series of variation from the time phase at which the blood flows in and the area of the coronary artery is maximum to the time phase at which the blood flows out and the area of the coronary artery is minimum as large as possible and less image motions (blurs) with the beating are desirably used.

Figure 4:
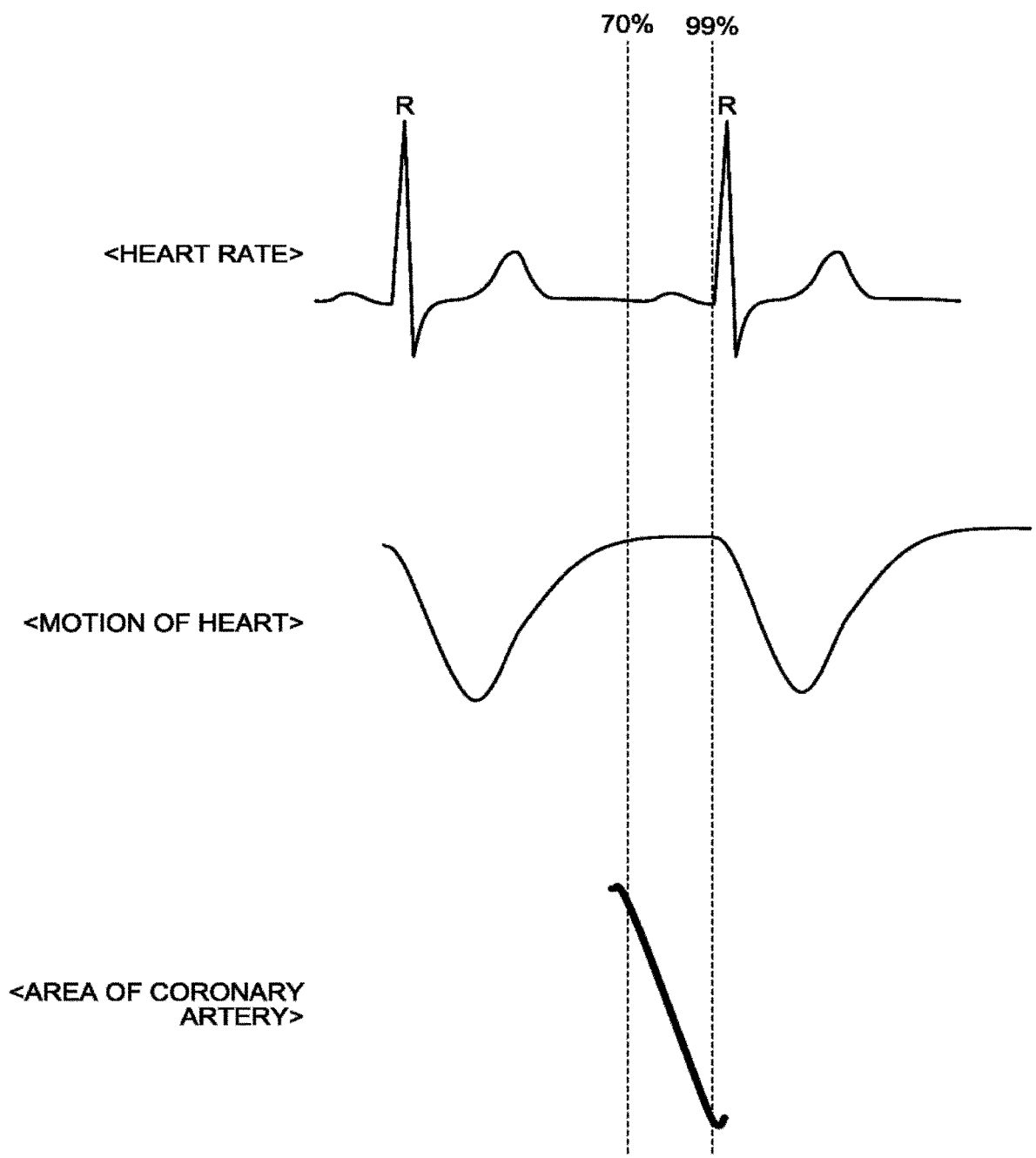
FIG. 4 is a view for explaining a plurality of time phases that are used for fluid analysis in the first embodiment.

FIG. 4 is a view for explaining the time phases that are used for the fluid analysis in the first embodiment. In FIG. 4, an upper stage indicates a heart rate, a middle stage indicates motion of the heart, and a lower stage indicates the area of the coronary artery. Furthermore, in FIG. 4, the horizontal direction indicates time, and temporal variations of the heart rate, the motion of the heart, and the area of the coronary artery are represented in a correspondence manner. The analysis function 355 executes the fluid analysis using the pieces of CT image data in cardiac phases that are contained in a cardiac phase range of 70% to 99%, for example. In the cardiac phase of 70% to 99%, the motion of the heart is less and the variation in the area of the coronary artery is large, as illustrated in FIG. 4. The heart moves with contraction and expansion and the motion thereof is stable in the latter half of a diastole (in the cardiac phase of 70% to 99%) as illustrated in the middle stage of FIG. 4. That is to say, the analysis function 355 can use the pieces of CT image data with less motion with the beating by using the pieces of CT image data in the cardiac phases that are contained in the cardiac phase range of 70% to 99% in which the motion of the heart is stable.

As illustrated in the lower stage of FIG. 4, the area of the coronary artery is maximum in the cardiac phase of around 70% and minimum in the cardiac phase of around 99%. This is because the blood starts flowing into the coronary artery in the cardiac phase of around 70%, and then, the blood flows out thereof toward the cardiac phase of 99%. The analysis function 355 can provide the analysis result with higher accuracy by using the pieces of CT image data in the cardiac phase range of 70% to 99% so as to involve the variation in the area of the coronary artery as large as possible.

In this manner, the analysis function 355 uses the pieces of CT image data corresponding to the cardiac phases in the fluid analysis for the coronary artery as the target. The analysis function 355 executes the fluid analysis using pieces of past CT image before surgery or in inspection in the follow-up after the surgery or after the inspection. To be specific, the analysis function 355 executes the fluid analysis for analyzing a state in the follow-up using the CT image data in one time phase that has been collected in the follow-up after the surgery or after the inspection and the pieces of past CT image data in the time phases. To be more specific, the registration function 352, the extraction function 353, and the image generation function 354, which will be described below, generate pieces of CT image data in the cardiac phases that simulate the state in the follow-up and the analysis function 355 executes the fluid analysis using the pieces of generated CT image data and the CT image in one time phase that has been collected in the follow-up. Hereinafter, details thereof will be described.

With reference to FIG. 2 again, the control function 351 controls the overall medical information processing apparatus 300. The control function 351 controls collection of the pieces of CT image data. To be specific, the control function 351 controls to collect pieces of past image data in a plurality of time phases that contain at least a part of the coronary artery of the heart and new image data in one time phase that contains at least a part of the coronary artery and has been acquired after acquisition of the pieces of past image data from the X-ray CT apparatus 100 or the image storage apparatus 200.

The registration function 352 executes registration processing between the pieces of CT image data in the cardiac phases that have been collected with time in the past and registration processing between the CT image data in one cardiac phase among the pieces of past CT image data in the cardiac phases and the new CT image data in one cardiac phase. To be more specific, the registration function 352 executes, for the pieces of past CT image data in the time phases, the registration processing between the past CT image data on which the registration processing with the new CT image data has been executed and the pieces of past CT image data other than the above-mentioned past CT image data.

FIG. 5 is a view for explaining an example of target images in the first embodiment. For example, as illustrated in FIG. 5, when pieces of CT image data (hereinafter, also referred to as past images) in the cardiac phases of "70%", "80%", "90%", and "99%" are used in the past fluid analysis (for example, before the surgery or in the inspection) and CT image data (hereinafter, also referred to as a current image) in the cardiac phase of "74%" is collected at the current time (for example, after the surgery or after the inspection), the registration function 352 executes the registration processing between the past images. The registration function 352 executes the registration processing between the past image data on which the registration processing with the current image is executed and the pieces of other past image data.

FIG. 6A is a view for explaining an example of the registration processing between the past images in the first embodiment. The registration function 352 executes the registration processing, for example, between the current image and the past image in the cardiac phase of "70%" that is the closest to the cardiac phase of "74%" among the past images because the cardiac phase of the newly collected current image is "74%". In this case, the registration function 352 executes the registration processing between the past image in the cardiac phase of "70%" and the other past images, as illustrated in FIG. 6A. That is to say, the registration function 352 executes the registration processing between the past image in the cardiac phase of "70%" and the past image in the cardiac phase of "80%", the registration processing between the past image in the cardiac phase of "70%" and the past image in the cardiac phase of "90%", and the registration processing between the past image in the cardiac phase of "70%" and the past image in the cardiac phase of "99%".

Figure 6B:
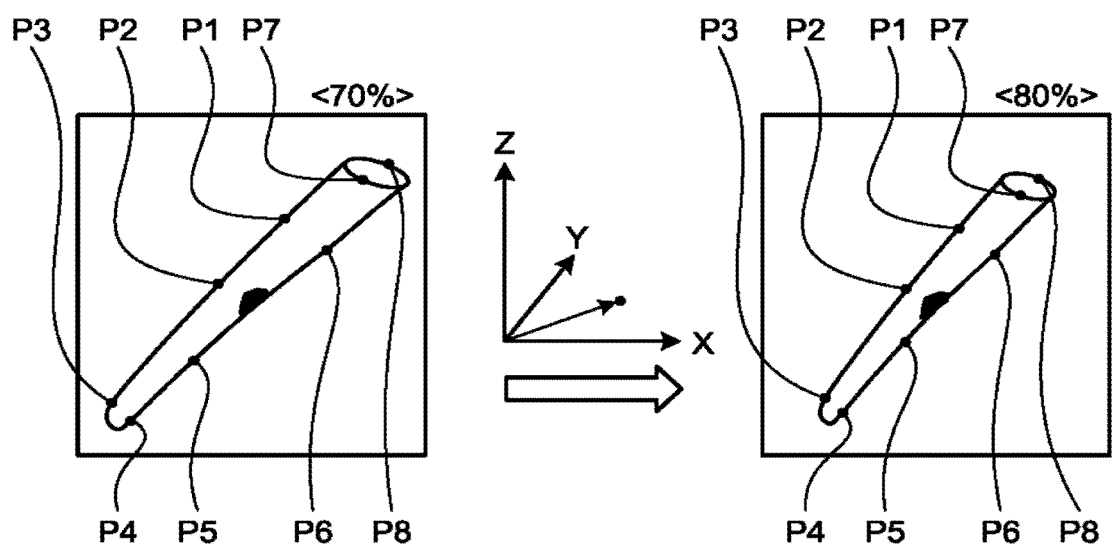
FIG. 6B is a view for explaining an example of the registration processing by a registration function in the first embodiment.

The registration function 352, for example, extracts correspondence points of the coronary artery from the respective pieces of CT image data on which the registration processing is performed, and executes non-rigid registration processing involving deformation so as to make the extracted correspondence points identical to each other. FIG. 6B is a view for explaining an example of the registration processing by the registration function 352 in the first embodiment. FIG. 6B illustrates the registration processing between the past image in the cardiac phase of "70%" and the past image in the cardiac phase of "80%". The registration function 352, for example, extracts correspondence points "P1" to "P8" from each of the past image in the cardiac phase of "70%" and the past image in the cardiac phase of "80%", as illustrated in FIG. 6B.

Then, the registration function 352 calculates pieces of coordinate conversion information for making the respective extracted correspondence points identical to each other. The registration function 352 calculates, for example, the pieces of coordinate conversion information in a three-dimensional coordinate system so as to make the correspondence points "P1" to "P8" in the past image in the cardiac phase of "70%" identical to the correspondence points "P1" to "P8" in the past image in the cardiac phase of "80%", respectively, as illustrated in FIG. 6B.

In the same manner, the registration function 352 executes the registration processing between the past image in the cardiac phase of "70%" and the past image in the cardiac phase of "90%" and the registration processing between the past image in the cardiac phase of "70%" and the past image in the cardiac phase of "99%" to calculate the pieces of coordinate conversion information.

Furthermore, the registration function 352 executes the registration processing between the past image and the current image. The registration function 352 executes the registration processing, for example, between the CT image data in the cardiac phase of "74%" for the newly collected current image and the CT image data in the cardiac phase of "70%" that is the closest cardiac phase among the past images. The registration function 352 executes the same processing as the above-mentioned non-rigid registration processing for the registration processing between the past image and the current image.

Figure 7:
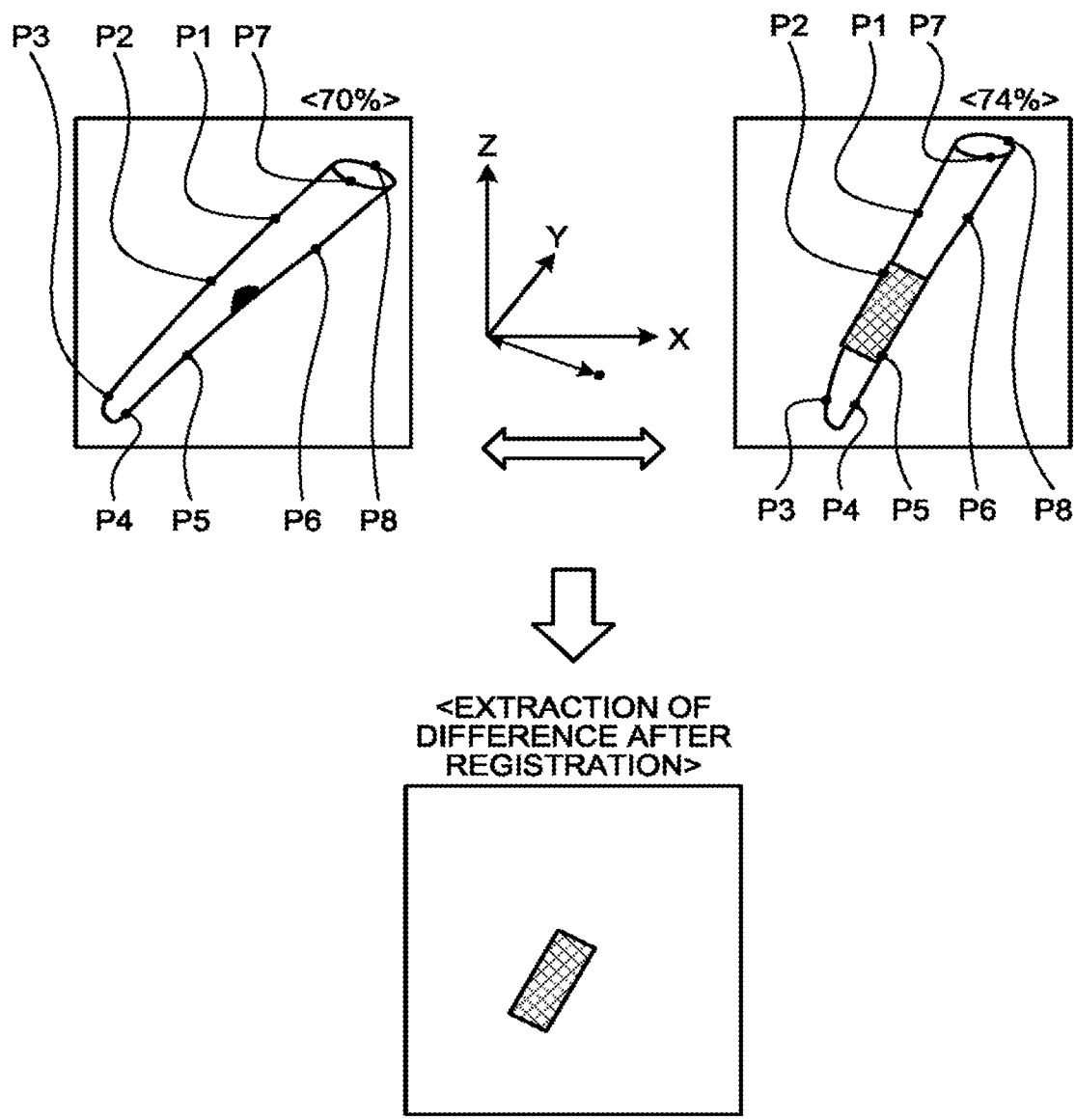
FIG. 7 is a view for explaining an example of processing by an extraction function in the first embodiment.

The extraction function 353 compares the past CT image data and the newly collected CT image data on which the registration processing has been executed to extract a differential region. That is to say, the extraction function 353 extracts difference between the past CT image data and the current CT image data on which the registration processing has been executed to extract a region (for example, treatment region) that has varied until the current time from the past. FIG. 7 is a view for explaining an example of processing by the extraction function 353 in the first embodiment. FIG. 7 illustrates the processing by the extraction function 353 after the correspondence points "P1" to "P8" are extracted from the past CT image data in the cardiac phase of "70%" and the current CT image data in the cardiac phase of "74%" and the non-rigid registration processing is executed. As illustrated in FIG. 7, the extraction function 353 extracts the difference between the pieces of CT image data on which the registration processing has been executed to extract a region of a stent left by treatment, for example.

The image generation function 354 generates pieces of generated image data corresponding to the time phases of the pieces of past CT image data other than the past CT image data on which the registration processing with the new CT image data has been executed based on the results of the registration processing. To be specific, the image generation function 354 generates the pieces of generated image data corresponding to the time phases of the pieces of past CT image data other than the past CT image data on which the registration processing with the new CT image data has been executed using the result of the registration processing between the new CT image data and the past CT image data and the results of the registration processing between the pieces of past CT image data.

The image generation function 354, for example, generates a current image in the cardiac phase of "80%" using the result of the registration processing between the past image in the cardiac phase of "70%" and the past image in the cardiac phase of "80%" and the result of the registration processing between the past image in the cardiac phase of "70%" and the current image in the cardiac phase of "74%". Furthermore, the image generation function 354 generates a current image in the cardiac phase of "90%" using the result of the registration processing between the past image in the cardiac phase of "70%" and the past image in the cardiac phase of "90%" and the result of the registration processing between the past image in the cardiac phase of "70%" and the current image in the cardiac phase of "74%". Moreover, the image generation function 354 generates a current image in the cardiac phase of "99%" using the result of the registration processing between the past image in the cardiac phase of "70%" and the past image in the cardiac phase of "99%" and the result of the registration processing between the past image in the cardiac phase of "70%" and the current image in the cardiac phase of "74%".

Figure 8:
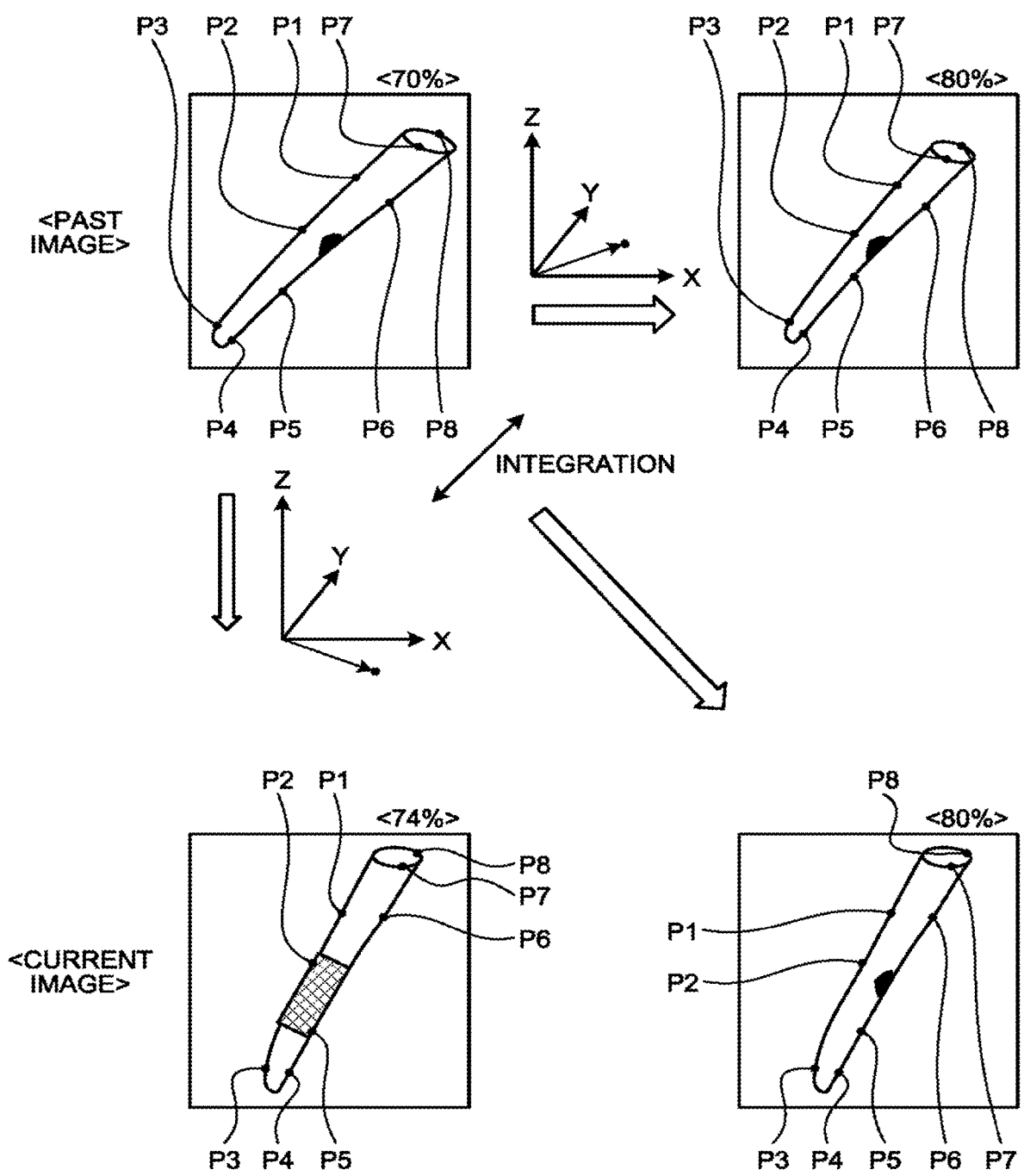
FIG. 8 is a view for explaining an example of image generation processing by an image generation function in the first embodiment.

FIG. 8 is a view for explaining an example of the image generation processing by the image generation function 354 in the first embodiment. FIG. 8 illustrates the case in which the current image in the cardiac phase of "80%" is generated using the result of the registration processing between the past image in the cardiac phase of "70%" and the past image in the cardiac phase of "80%" and the result of the registration processing between the past image in the cardiac phase of "70%" and the current image in the cardiac phase of "74%". For example, the image generation function 354 generates the current image in the cardiac phase of "80%" by deforming the past image in the cardiac phase of "70%" using pieces of coordinate conversion information provided by integrating the pieces of coordinate conversion information in the three-dimensional coordinate system for making the correspondence points "P1" to "P8" in the past image in the cardiac phase of "70%" identical to the correspondence points "P1" to "P8" in the past image in the cardiac phase of "80%" and the pieces of coordinate conversion information in the three-dimensional coordinate system for making the correspondence points "P1" to "P8" in the past image in the cardiac phase of "70%" identical to the correspondence points "P1" to "P8" in the current image of "74%", as illustrated in FIG. 8.

In the same manner, the image generation function 354 generates the current image in the cardiac phase of "90%" and the current image in the cardiac phase of "99%". Then, the image generation function 354 generates pieces of CT image data provided by synthesizing the differential region extracted by the extraction function 353 with the generated current images in the respective cardiac phases. For example, the image generation function 354 specifies a position (coordinates) of the differential region in the generated current image in the cardiac phase of "80%" and generates the current CT image data in the cardiac phase of "80%" in which the specified position is replaced by the differential region. Furthermore, the image generation function 354 specifies a position (coordinates) of the differential region in the generated current image in the cardiac phase of "90%" and generates the current CT image data in the cardiac phase of "90%" in which the specified position is replaced by the differential region. Moreover, the image generation function 354 specifies a position (coordinates) of the differential region in the generated current image in the cardiac phase of "99%" and generates the current CT image data in the cardiac phase of "99%" in which the specified position is replaced by the differential region.

Figure 9:
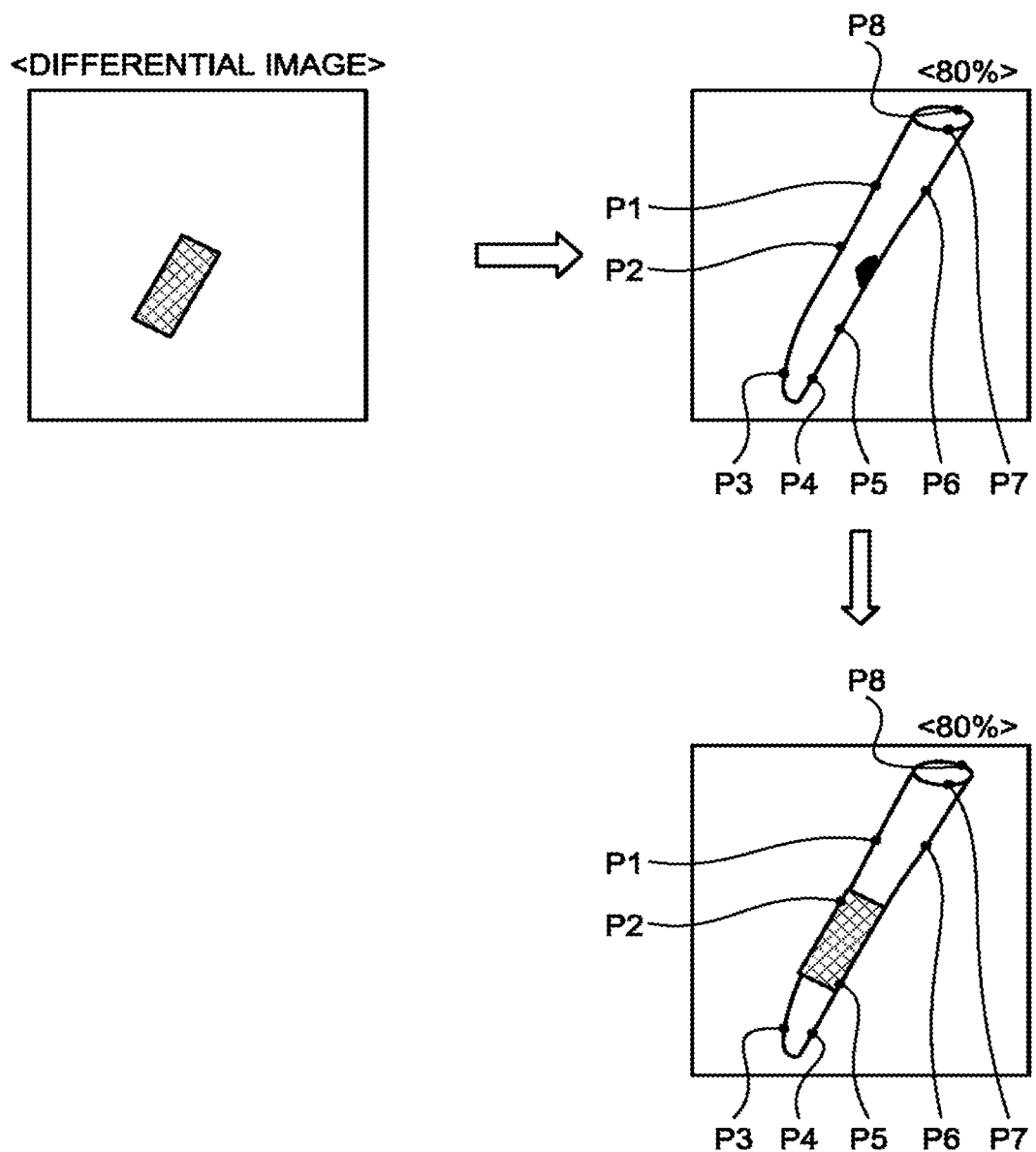
FIG. 9 is a view for explaining an example of correction processing by the image generation function in the first embodiment.

When the differential region contains the stent, the image generation function 354 corrects the regions corresponding to the differential region in the pieces of generated current CT image data in accordance with the size of the stent. The image generation function 354, for example, further deforms vascular walls in the respective pieces of CT image data so as to maintain the cross-sectional area of the stent. FIG. 9 is a view for explaining an example of correction processing by the image generation function 354 in the first embodiment. When the differential region contains the stent, as illustrated in FIG. 9, the image generation function 354 corrects the vascular wall in the current image in the cardiac phase of "80%" in accordance with the size of the stent in the differential image.

As an example, the image generation function 354 specifies a position of the stent in the current image in the cardiac phase of "80%" and deforms the vascular wall making contact with the specified position in accordance with the size of the stent. In the same manner, the image generation function 354 also deforms the vascular wall in accordance with the size of the stent in each of the current image in the cardiac phase of "90%" and the current image in the cardiac phase of "99%".

The analysis function 355 executes the fluid analysis using the pieces of CT image data provided by synthesizing the differential region with the pieces of CT image data. For example, the analysis function 355 executes the fluid analysis using the current CT image data in the cardiac phase of "80%" that contains the differential region, the current CT image data in the cardiac phase of "90%" that contains the differential region, and the current CT image data in the cardiac phase of "99%" that contains the differential region. The new CT image data may be used as it is or the past CT image data in the cardiac phase of "70%" may be used for the current CT image data in the cardiac phase of "74%". When the past CT image data in the cardiac phase of "70%" is used, CT image data generated by executing the registration processing on the past CT image data in the cardiac phase of "70%" so as to make it identical to the current CT image data in the cardiac phase of "74%" and performing replacement by the differential region is used.

Figure 10:
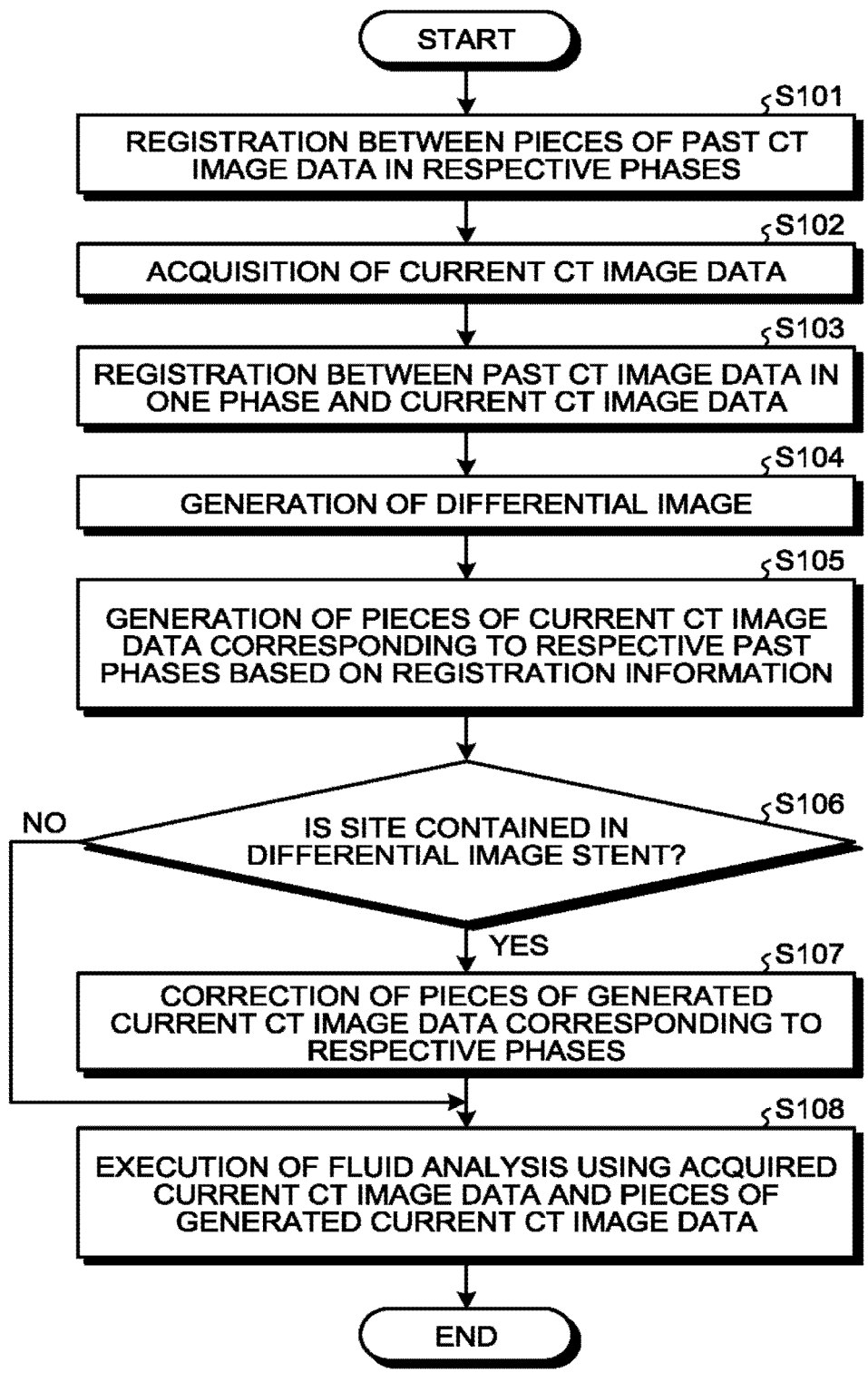
FIG. 10 is a flowchart illustrating processing procedure by the medical information processing apparatus in the first embodiment.

Next, procedures of the processing by the medical information processing apparatus 300 in the first embodiment will be described. FIG. 10 is a flowchart illustrating the processing procedures by the medical information processing apparatus 300 in the first embodiment. Step S101 to step S103 in FIG. 10 are implemented by, for example, calling a computer program corresponding to the registration function 352 from the memory circuitry 320 for execution by the processing circuitry 350. Step S104 is implemented by, for example, calling a computer program corresponding to the extraction function 353 from the memory circuitry 320 for execution by the processing circuitry 350. Step S105 to step S107 are implemented by, for example, calling a computer program corresponding to the image generation function 354 from the memory circuitry 320 for execution by the processing circuitry 350. Step S108 is implemented by, for example, calling a computer program corresponding to the analysis function 355 from the memory circuitry 320 for execution by the processing circuitry 350.

In the medical information processing apparatus 300 in the embodiment, first, the processing circuitry 350 executes the registration processing between the pieces of past CT image data in the cardiac phases (step S101). Then, the processing circuitry 350 acquires the current CT image data (step S102), and executes the registration processing between the past CT image data in one phase and the current CT image data (step S103). Thereafter, the processing circuitry 350 differentiates the past CT image data and the current CT image data on which the registration processing has been executed to generate a differential image (step S104).

Then, the processing circuitry 350 generates the pieces of current CT image data corresponding to the respective past cardiac phases based on pieces of registration information (step S105), and determines whether a site contained in the differential image is a stent (step S106). When the site contained in the differential image is the stent (Yes at step S106), the processing circuitry 350 corrects the pieces of generated current CT image data corresponding to the respective cardiac phases (step S107).

Subsequently, the processing circuitry 350 executes the fluid analysis using the acquired current CT image data and the pieces of generated current CT image data (step S108). When the site contained in the differential image is not the stent at step S106 (No at step S106), the processing circuitry 350 proceeds to step S108 and executes the fluid analysis using the acquired current CT image data and the pieces of generated current CT image data (step S108).

As described above, according to the first embodiment, the registration function 352 executes the registration processing between the pieces of past CT image data in the time phases that have been collected with time and the registration processing between the past CT image data in one time phase among the pieces of past CT image data in the time phases and the new CT image data in one time phase. The extraction function 353 compares the past CT image data and the new CT image data on which the registration processing has been executed to extract the differential region. The image generation function 354 generates the pieces of CT image data corresponding to the time phases of the pieces of past CT image data other than the past CT image data on which the registration processing with the new CT image data has been executed based on the results of the registration processing. The analysis function 355 executes the fluid analysis using the pieces of CT image data provided by synthesizing the differential region. Accordingly, the medical information processing apparatus 300 in the first embodiment can reduce the image collection in the follow-up to that for one time phase, thereby reducing the exposure dose in the follow-up.

According to the first embodiment, the registration function 352 executes, for the pieces of past CT image data in the time phases, the registration processing between the past CT image data on which the registration processing with the new CT image data has been executed and the pieces of past CT image data other than the above-mentioned past CT image data. The image generation function 354 generates the pieces of CT image data corresponding to the time phases of the pieces of past CT image data other than the past CT image data on which the registration processing with the new CT image data has been executed using the result of the registration processing between the new CT image data and the past CT image data and the results of the registration processing between the pieces of past CT image data. Accordingly, the medical information processing apparatus 300 in the first embodiment can easily generate the pieces of current CT image data corresponding to the cardiac phases of the pieces of past CT image data.

Moreover, according to the first embodiment, when the differential region contains the stent, the image generation function 354 corrects the regions corresponding to the differential region in the pieces of CT image data in accordance with the size of the stent. Accordingly, the medical information processing apparatus 300 in the first embodiment can execute the fluid analysis with high accuracy.

Second Embodiment

Although the first embodiment has been described hereinabove, the disclosure may be carried out in various different modes other than the above-mentioned first embodiment.

In the above-mentioned embodiment, the newly collected CT image data is used as the current CT image data. The embodiment is not, however, limited thereto and, for example, the current CT image data may be generated based on past CT image data. In this case, the image generation function 354 generates the current CT image data by, for example, predicting a current state of the coronary artery based on information related to progress after treatment and deforming the past CT image data to be compatible with the predicted state.

Furthermore, in the above-mentioned embodiment, registration between one of the past images and the current image is executed. The embodiment is not, however, limited thereto and, for example, registration between all of the past images and the current image may be executed. For example, in addition to the registration between the current image in the cardiac phase of "74%" and the past image in the cardiac phase of "70%, registration between the current image in the cardiac phase of "74%" and the past image in the cardiac phase of "80%", registration between the current image in the cardiac phase of "74%" and the past image in the cardiac phase of "90%", and registration between the current image in the cardiac phase of "74%" and the past image in the cardiac phase of "99%" may be executed. In this case, the extraction function 353 extracts differential regions from the respective pieces of CT image data after registration.

In the above-mentioned embodiment, the differential region between the past image and the current image is extracted and the extracted differential region is synthesized. The embodiment is not, however, limited thereto and, for example, the differential region may not be extracted. In this case, the image generation function 354, for example, generates the pieces of CT image data corresponding to the time phases of the pieces of past CT image data other than the past CT image data on which the registration processing with the new CT image data has been executed using the result of the registration processing between the new CT image data and the past CT image data and the results of the registration processing between the pieces of past CT image data.

The image generation function 354 generates, for example, the CT image data of the current image in the cardiac phase of "80%" by deforming the CT image data of the past image in the cardiac phase of "70%" using pieces of coordinate conversion information provided by integrating the pieces of coordinate conversion information in the three-dimensional coordinate system for making the correspondence points in the past image in the cardiac phase of "70%" identical to the correspondence points in the past image in the cardiac phase of "80%" and the pieces of coordinate conversion information in the three-dimensional coordinate system for making the correspondence points in the past image in the cardiac phase of "70%" identical to the correspondence points in the current image of "74%". In the same manner, the image generation function 354 generates the pieces of CT image data in the other cardiac phases. The analysis function 355 executes the fluid analysis using the pieces of generated CT image data.

In the above-mentioned embodiment, the stent is left in the blood vessel, as an example. The embodiment is not, however, limited thereto and pieces of CT image data before and after various procedures can be set to the targets. For example, the medical information processing apparatus 300 executes the above-mentioned pieces of processing on pieces of CT image data in a plurality of time phases that have been collected before a procedure such as pharmacological treatment, directional coronary atherectomy (DCA), and rotational coronary atherectomy and CT image data in one time phase that has been collected after the above-mentioned procedure. In this case, the extraction function 353 extracts a region having a shape deformed by the above-mentioned procedure as the differential region. Then, the image generation function 354 generates pieces of CT image data provided by synthesizing the extracted differential region. Furthermore, the analysis function 355 executes the fluid analysis using the pieces of generated CT image data.

Figure 11:
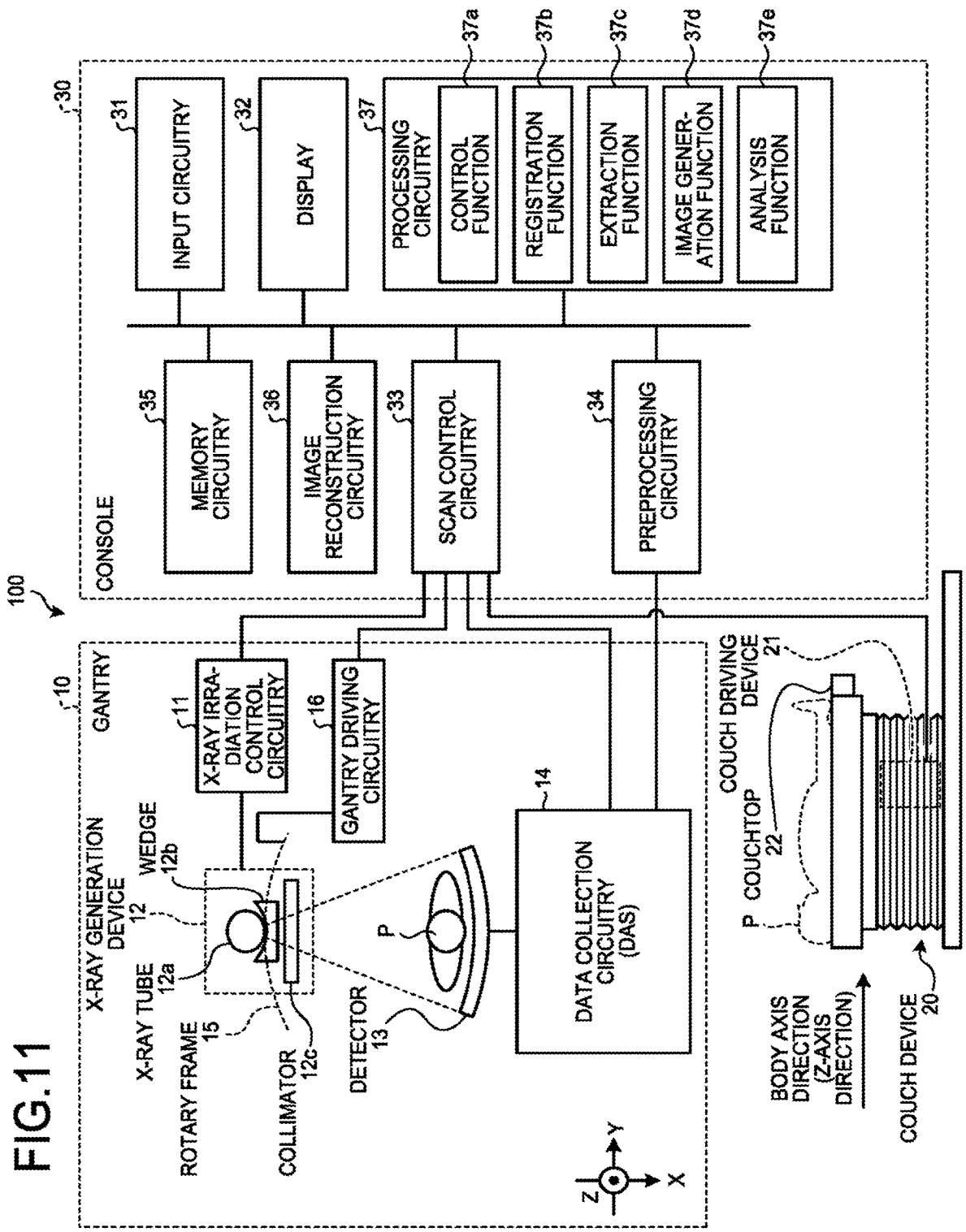
FIG. 11 is a diagram illustrating an example of the configuration of an X-ray CT apparatus according to a second embodiment.

In the above-mentioned embodiment, the medical information processing apparatus 300 executes various pieces of processing. The embodiment is not, however, limited thereto and, for example, the X-ray CT apparatus 100 may execute various pieces of processing. FIG. 11 is a diagram illustrating an example of the configuration of the X-ray CT apparatus 100 in the second embodiment.

As illustrated in FIG. 11, the X-ray CT apparatus 100 in the second embodiment includes a gantry 10, a couch device 20, and a console 30. The gantry 10 is a device irradiating a subject P (patient) with X rays, detecting the X rays that have passed through the subject P, and outputting the X rays to the console 30, and includes an X-ray irradiation control circuitry 11, an X-ray generation device 12, a detector 13, a data collection circuitry (data acquisition system (DAS)) 14, a rotary frame 15, and a gantry driving circuitry 16.

The rotary frame 15 is a circular ring-shaped frame that supports the X-ray generation device 12 and the detector 13 so that they oppose each other with the subject P interposed therebetween, and rotates at high speed along a circular trajectory about the subject P by the gantry driving circuitry 16, which will be described later.

The X-ray irradiation control circuitry 11 is a device that, as a high-voltage generation unit, supplies a high voltage to an X-ray tube 12a, and the X-ray tube 12a generates X rays using the high voltage supplied from the X-ray irradiation control circuitry 11. The X-ray irradiation control circuitry 11 adjusts a dose of the X rays that are emitted to the subject P by adjusting a tube voltage and a tube current that are supplied to the X-ray tube 12a under control by scan control circuitry 33, which will be described later.

The X-ray irradiation control circuitry 11 switches a wedge 12b. The X-ray irradiation control circuitry 11 adjusts an emission range (a fan angle and a cone angle) of the X rays by adjusting the aperture of a collimator 12c. It should be noted that the embodiment may be applied to the case in which an operator manually switches a plurality of types of wedges.

The X-ray generation device 12 is a device that generates the X rays and emits the generated X rays to the subject P, and includes the X-ray tube 12a, the wedge 12b, and the collimator 12c.

The X-ray tube 12a is a vacuum tube for emitting X-ray beams to the subject P with the high voltage supplied by the high-voltage generation unit (not illustrated), and emits the X-ray beams to the subject P with rotation of the rotary frame 15. The X-ray tube 12a generates the X-ray beams spreading with the fan angle and the cone angle. For example, the X-ray tube 12a can continuously expose the subject P to the X rays at the whole circumference of the subject P for full reconstruction or can continuously expose the subject P to the X rays in an exposure range (180 degrees+fan angle) enabling half reconstruction for the half reconstruction under control by the X-ray irradiation control circuitry 11. The X-ray tube 12a can intermittently expose the subject P to the X rays (pulse X rays) at preset positions (tube bulb positions) under control by the X-ray irradiation control circuitry 11. The X-ray irradiation control circuitry 11 can modulate the intensity of the X rays that are emitted from the X-ray tube 12a. The X-ray irradiation control circuitry 11 increases the intensity of the X rays that are emitted from the X-ray tube 12a at a specified tube bulb position and decreases the intensity of the X rays that are emitted from the X-ray tube 12a in a range other than the specified tube bulb position, for example.

The wedge 12b is an X-ray filter for adjusting the X-ray dose of the X rays emitted from the X-ray tube 12a. To be specific, the wedge 12b is a filter transmitting and attenuating the X rays emitted from the X-ray tube 12a so as to cause the X ray emitted from the X-ray tube 12a to the subject P to have predetermined distribution. The wedge 12b is, for example, a filter provided by processing aluminum to have a predetermined target angle and a predetermined thickness. It should be noted that the wedge 12b is also referred to as a wedge filter (wedge filter) or a bow-tie filter.

The collimator 12c is a slit for narrowing an emission range of the X rays the X-ray dose of which has been adjusted by the wedge 12b under control by the X-ray irradiation control circuitry 11, which will be described later.

The gantry driving circuitry 16 rotationally moves the X-ray generation device 12 and the detector 13 on the circular trajectory about the subject P by rotationally driving the rotary frame 15.

The detector 13 is a two-dimensional array detector (surface detector) for detecting the X rays that have passed through the subject P and a plurality of detection element rows formed by arranging X-ray detection elements for a plurality of channels are aligned in the detector 13 along a body axis direction of the subject P (Z-axis direction illustrated in FIG. 11). To be specific, the detector 13 in the second embodiment includes the X-ray detection elements aligned in multiple rows as much as 320 rows along the body axis direction of the subject P, and can detect the X rays that have passed through the subject P in a wide range such as a range including the lungs and the heart of the subject P.

The data collection circuitry 14 is a DAS, and collects pieces of projection data from the pieces of X-ray detection data detected by the detector 13. For example, the data collection circuitry 14 performs amplification processing, A-to-D conversion processing, sensitivity correction processing between channels, and the like on the X-ray intensity distribution data detected by the detector 13 to generate the pieces of projection data, and transmits the pieces of generated projection data to the console 30, which will be described later. When the X-ray tube 12a continuously emits the X rays during the rotation of the rotary frame 15, for example, the data collection circuitry 14 collects a projection data group for the whole circumference (360 degrees). The data collection circuitry 14 transmits the pieces of collected projection data related to tube bulb positions to the console 30, which will be described later. The tube bulb positions are pieces of information indicating projection directions of the pieces of projection data. It should be noted that preprocessing circuitry 34, which will be described later, may perform the sensitivity correction processing between the channels.

The couch device 20 is a device on which the subject P is placed, and includes a couch driving device 21 and a couchtop 22, as illustrated in FIG. 11. The couch driving device 21 moves the couchtop 22 in the Z-axis direction to move the subject P into the rotary frame 15. The couchtop 22 is a plate on which the subject P is placed.

The gantry 10 executes helical scan that scans the subject P in a spiral manner by rotating the rotary frame 15 while moving the couchtop 22, for example. Alternatively, the gantry 10 executes conventional scan that scans the subject P along a circular trajectory by rotating the rotary frame 15 while keeping the position of the subject P after moving the couchtop 22. The gantry 10 executes a step-and-shoot system that performs the conventional scan in a plurality of scan areas by moving the position of the couchtop 22 at a constant interval.

The console 30 is a device that receives an operation on the X-ray CT apparatus 100 by the operator and reconstructs CT image data using the pieces of projection data collected by the gantry 10. The console 30 includes, as illustrated in FIG. 11, input circuitry 31, a display 32, scan control circuitry 33, the preprocessing circuitry 34, memory circuitry 35, image reconstruction circuitry 36, and processing circuitry 37.

The input circuitry 31 includes a mouse, a keyboard, a trackball, a switch, a button, or a joystick that is used for inputting various instructions and various settings by the operator of the X-ray CT apparatus 100, and transmits pieces of information of the instructions and the settings received from the operator to the processing circuitry 37. The input circuitry 31 receives, for example, shooting conditions of CT image data, reconstruction conditions when the CT image data is reconstructed, image processing conditions on the CT image data, and the like from the operator. The input circuitry 31 receives an operation for selecting inspection on the subject P. The input circuitry 31 further receives a specification operation for specifying a site on an image.

The display 32 is a monitor that the operator checks, and displays image data generated from the CT image data to the operator and displays a graphical user interface (GUI) for receiving various instructions, various settings, and the like from the operator through the input circuitry 31 under control by the processing circuitry 37. Furthermore, the display 32 displays a plan screen of a scan plan, a screen during scan, and the like.

The scan control circuitry 33 controls the collection processing of the pieces of projection data in the gantry 10 by controlling operations of the X-ray irradiation control circuitry 11, the gantry driving circuitry 16, the data collection circuitry 14, and the couch driving device 21 under control by the processing circuitry 37. To be specific, the scan control circuitry 33 controls collection processing of the pieces of projection data in shooting for collecting positioning images (scanogram images) and actual shooting (scan) for collecting images that are used for diagnosis.

The preprocessing circuitry 34 performs logarithmic conversion processing and pieces of correction processing such as offset correction, sensitivity correction, and beam hardening correction on the pieces of projection data generated by the data collection circuitry 14 to generate pieces of corrected projection data. To be specific, the preprocessing circuitry 34 generates the pieces of corrected projection data for the pieces of projection data of the positioning images and the pieces of projection data collected by the actual shooting that have been generated by the data collection circuitry 14, and stores them in the memory circuitry 35.

The memory circuitry 35 stores therein the pieces of projection data generated by the preprocessing circuitry 34. To be specific, the memory circuitry 35 stores therein the pieces of projection data of the positioning images and the pieces of projection data for diagnosis collected by the actual shooting that have been generated by the preprocessing circuitry 34. The memory circuitry 35 stores therein pieces of CT image data reconstructed by the image reconstruction circuitry 36, which will be described later, and the like. The memory circuitry 35 appropriately stores therein a processing result by the processing circuitry 37, which will be described later.

The image reconstruction circuitry 36 reconstructs the pieces of CT image data using the pieces of projection data stored in the memory circuitry 35. To be specific, the image reconstruction circuitry 36 reconstructs the pieces of CT image data from the pieces of projection data of the positioning images and the pieces of projection data of the images that are used for diagnosis. There are various methods as the reconstruction method and examples thereof include an inverse projection process. Furthermore, examples of the inverse projection process include an inverse projection process by a filtered back projection method (FEP). Alternatively, the image reconstruction circuitry 36 can also reconstruct the pieces of CT image data using a successive approximation method.

The image reconstruction circuitry 36 performs various pieces of image processing on the pieces of CT image data to generate pieces of image data. Then, the image reconstruction circuitry 36 stores the pieces of reconstructed CT image data and the pieces of image data generated by various pieces of image processing in the memory circuitry 35.

The processing circuitry 37 controls the overall X-ray CT apparatus 100 by controlling the operations of the gantry 10, the couch device 20, and the console 30. To be specific, the processing circuitry 37 controls CT scan that is performed in the gantry 10 by controlling the scan control circuitry 33. The processing circuitry 37 controls the image reconstruction processing and the image generation processing in the console 30 by controlling the image reconstruction circuitry 36. The processing circuitry 37 controls various pieces of image data stored in the memory circuitry 35 to be displayed on the display 32.

The processing circuitry 37 executes, as illustrated in FIG. 11, a control function 37a, a registration function 37b, an extraction function 37c, an image generation function 37d, and an analysis function 37e. The control function 37a controls the overall X-ray CT apparatus 100. The registration function 37b executes the same processing as the above-mentioned registration function 352. The extraction function 37c executes the same processing as the above-mentioned extraction function 353. The image generation function 37d executes the same processing as the above-mentioned image generation function 354. The analysis function 37e executes the same processing as the above-mentioned analysis function 355.

Although in the above-mentioned embodiments, the single processing circuitry (the processing circuitry 350 and the processing circuitry 37) implement the respective processing functions, as an example, the embodiment is not limited thereto. The processing circuitry 350 and the processing circuitry 37 may be configured by combining a plurality of independent processors and the processors may respectively execute the computer programs to implement the respective processing functions. Alternatively, the respective processing functions of the processing circuitry 350 and the processing circuitry 37 may be appropriately separated or integrated into a single or a plurality of processing circuit(s) to be implemented.

The expression "processor" used in the above-mentioned respective embodiments indicates, for example, a central processing unit (CPU), a graphics processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). The computer programs may be directly embedded in the circuit of the processor instead of storage of the computer programs in the memory circuitry. In this case, the processor reads and executes the computer programs embedded in the circuit to implement the functions. Furthermore, each processor in the embodiment is not limited to be configured by a single circuit and a plurality of independent circuits may be combined to configure one processor and implement the functions thereof.

The computer programs that are executed by the processor are embedded and provided in a read only memory (ROM), a memory circuit, or the like. The computer programs may be recorded and provided in a computer-readable recording medium such as a compact disc (CD)-ROM, a flexible disk (FD), a CD-recordable (R), and a digital versatile disc (DVD), as an installable or executable file. The computer programs may be stored in a computer connected to a network such as the Internet and provided or distributed by being downloaded via the network. The computer programs are configured by, for example, modules including respective function, which will be described later. As actual hardware, the CPU reads and executes the computer programs from a storage medium such as the ROM to cause the respective modules to be loaded and generated on a main storage device.

At least one of the above-mentioned embodiments can reduce an exposure dose in the follow-up.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising:
   processing circuitry configured to
      collect a plurality of images corresponding to a plurality of time phases, wherein the plurality of images represent at least a part of a coronary artery of a heart and include (a) a first image corresponding to a first time phase of the plurality of time phases and (b) other images corresponding to other time phases of the plurality of time phases;
      collect a subsequent image at a subsequent time phase, wherein the subsequent image represents at least the part of the coronary artery and has been acquired after acquisition of the plurality of images, and wherein the subsequent time phase corresponds most closely, as between the first time phase and the other time phases, to the first time phase;
      perform first registration processing between the first image and the other images;
      perform second registration processing between the first image and the subsequent image;
      generate a plurality of synthesized images corresponding to the other time phases based on results of the first registration processing and the second registration processing; and
      derive a fluid parameter related to the coronary artery by executing fluid analysis using at least one of the plurality of synthesized images.

2. The medical information processing apparatus according to claim 1, wherein
   a first synthesized image of the plurality of synthesized images is produced by deforming a shape of the coronary artery in the first image based on a procedure, and
   the processing circuitry is configured to extract a differential region having a shape which has been deformed by the procedure.

3. The medical information processing apparatus according to claim 2, wherein when the differential region contains a stent, the processing circuitry is configured to correct the differential region in the plurality of synthesized images in accordance with a size of the stent.

4. The medical information processing apparatus according to claim 1, wherein the processing circuitry is further configured to extract a differential region by comparing the first image and the subsequent image, and
   wherein the processing circuitry configured to generate the synthesized images comprises processing circuitry configured to generate the plurality of synthesized images for the differential region at time phases corresponding to the other time phases.

5. The medical information processing apparatus according to claim 1, wherein the plurality of synthesized images is generated by deforming the other images.

6. The medical information processing system according to claim 1, wherein the plurality of images is collected before a medical procedure, and the subsequent image is collected after the medical procedure.

7. The medical information processing system according to claim 6, wherein the medical procedure comprises insertion of a stent into the coronary artery represented in the plurality of images.

8. The medical information processing system according to claim 1, wherein processing circuitry configured to perform the first registration processing comprises processing circuitry configured to detect plural correspondence points in each of the first and other images and register the first and other images using the detected correspondence points.

9. The medical information processing system according to claim 8, wherein processing circuitry configured to perform the second registration processing comprises processing circuitry configured to detect plural correspondence points in the subsequent image and register the first and subsequent images using the detected correspondence points.

10. An X-ray CT apparatus comprising:
an X-ray generation device;
an X-ray detector; and
processing circuitry configured to
collect a plurality of images corresponding to a plurality of time phases, wherein the plurality of images represent at least a part of a coronary artery of a heart and include (a) a first image corresponding to a first time phase of the plurality of time phases and (b) other images corresponding to other time phases of the plurality of time phases;
collect a subsequent image at a subsequent time phase, wherein the subsequent image represents at least the part of the coronary artery and has been acquired after acquisition of the plurality of images, and wherein the subsequent time phase corresponds most closely, as between the first time phase and the other time phases, to the first time phase;
perform first registration processing between the first image and the other images;
perform second registration processing between the first image and the subsequent image;
generate a plurality of synthesized images corresponding to the other time phases based on results of the first registration processing and the second registration processing; and
derive a fluid parameter related to the coronary artery by executing fluid analysis using at least one of the plurality of synthesized images.

11. A medical information processing method comprising:
collecting a plurality of images corresponding to a plurality of time phases, wherein the plurality of images represent at least a part of a coronary artery of a heart and include (a) a first image corresponding to a first time phase of the plurality of time phases and (b) other images corresponding to other time phases of the plurality of time phases;
collecting a subsequent image at a subsequent time phase corresponding to the first time phase, wherein the subsequent image represents at least the part of the coronary artery and has been acquired after acquisition of the plurality of images, and wherein the subsequent time phase corresponds most closely, as between the first time phase and the other time phases, to the first time phase;
performing first registration processing between the first image and the other images;
performing second registration processing between the first image and the subsequent image;
generating a plurality of synthesized images corresponding to the other time phases based on results of the first registration processing and the second registration processing; and
deriving a fluid parameter related to the coronary artery by executing fluid analysis using the plurality of synthesized images.

* * * * *